United States Patent [19]

Pfleger

[11] 4,305,526
[45] Dec. 15, 1981

[54] DEVICE FOR DISPENSING ARTICLES FROM A BOXED STACK

[76] Inventor: Frederick W. Pfleger, 27 Cherry Ave., Maple Shade, N.J. 08052

[21] Appl. No.: 120,688

[22] Filed: Feb. 11, 1980

[51] Int. Cl.³ ............................................. B65H 3/24
[52] U.S. Cl. .................................... 221/197; 221/256
[58] Field of Search ............... 221/197, 233, 234, 235, 221/256, 257, 266, 198

[56] References Cited

U.S. PATENT DOCUMENTS

| 1,057,322 | 3/1913 | Bowman | 221/256 X |
| 1,751,169 | 3/1930 | Parker | 221/197 X |
| 2,311,632 | 2/1943 | Berger et al. | 221/266 X |
| 4,173,211 | 11/1979 | Crawford | 221/266 X |

FOREIGN PATENT DOCUMENTS 2447606  4/1975  Fed. Rep. of Germany ...... 221/266

Primary Examiner—F. J. Bartuska
Attorney, Agent, or Firm—Robert K. Youtie

[57] ABSTRACT

An upwardly opening receiver for receiving the lower open end of a box containing articles to be dispensed, an article carrier shiftable transversely through a lower region of the receiver, and a pusher on the carrier for pushing engagement with the lowermost article upon carrier movement to dispense the article exteriorly of the receiver.

4 Claims, 4 Drawing Figures

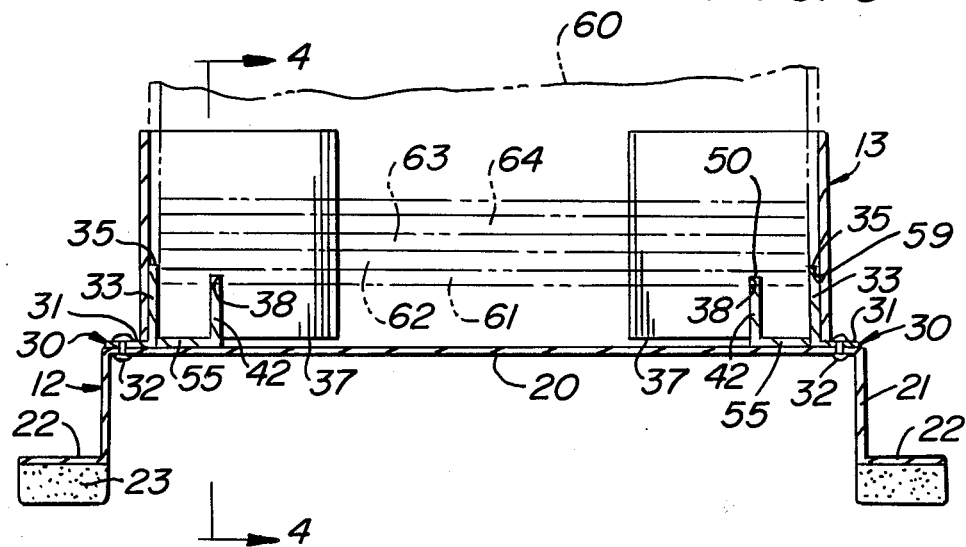

DEVICE FOR DISPENSING ARTICLES FROM A BOXED STACK

BACKGROUND OF THE INVENTION

This invention is concerned with dispensing laboratory slides directly from a box in a simple and expeditious manner, without undue soiling, handling or breakage of the slides. Heretofore it was necessary to empty a quantity of laboratory slides from their container into a dispenser to achieve the desired dispensing, but this required tedious and time consuming handling, often resulting in soiling and damage.

While the art of dispensing the lowermost article from a stack is crowded and highly developed, the requisites for dispensing slides from a box have not been satisfactorily met by the prior art.

The prior patents of which applicant is aware are as follows:
U.S. PAT. NOS.
300,715;
1,138,075;
1,419,075;
2,119,912;
2,439,550;
2,635,026;
2,707,066;
3,095,117;
3,193,139;
3,298,568.

SUMMARY OF THE INVENTION

Accordingly, it is an important object of the present invention to provide a dispensing device, particularly for dispensing slides from a boxed stack, which is extremely simple in construction and operation, reliably presents a single slide for convenient, safe and clean removal, and is trouble free throughout a long useful life.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 3 is a sectional elevational view taken generally along the line 3—3 of FIG. 2, and illustrating in phantom a box of slides in operative association with the dispenser.

FIG. 4 is a sectional elevational view taken generally along the line 4—4 of FIG. 3.

DESCRIPTION OF THE PREFERRED EMBODIMENT

Figure 1:
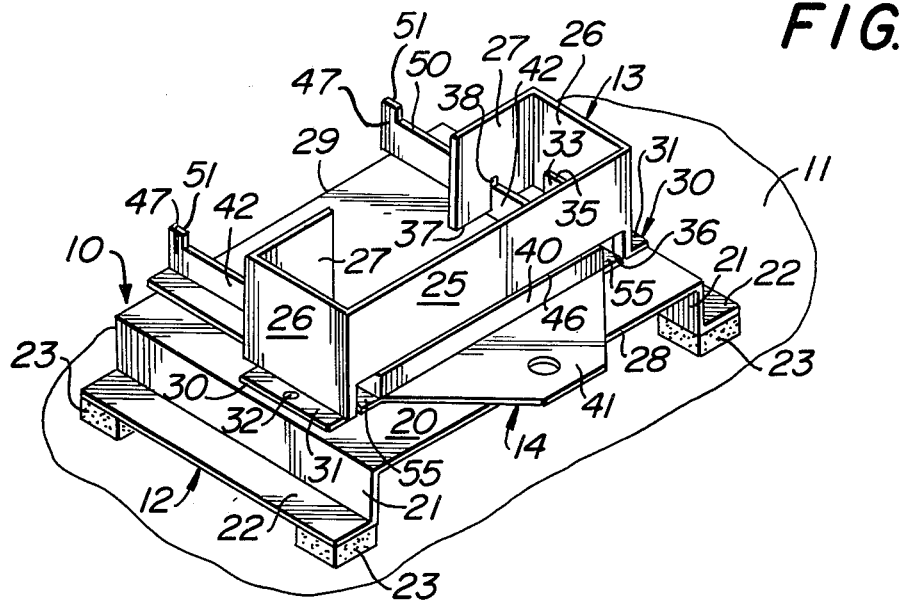
FIG. 1 is a top perspective view showing a dispensing device of the present invention, with a slide carrier in retracted position.
Figure 2:
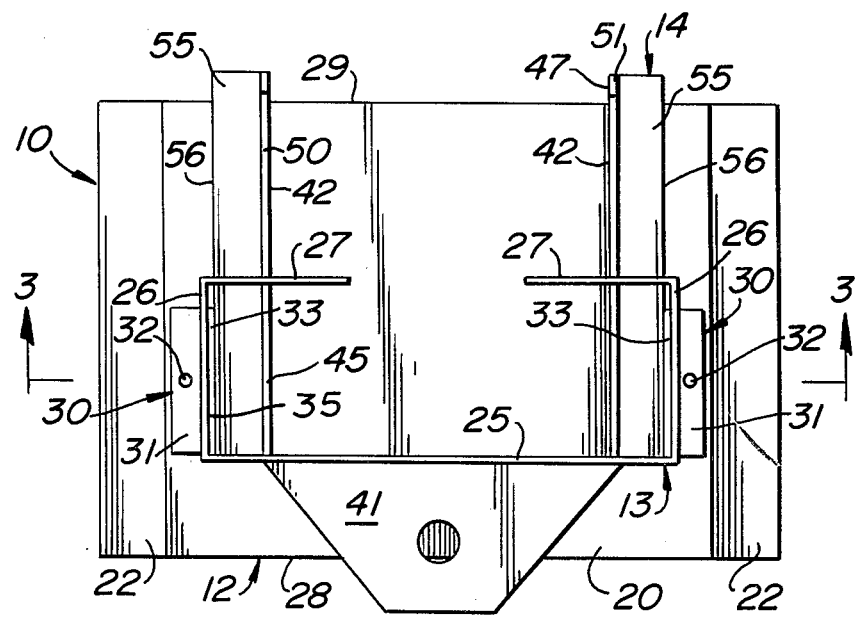
FIG. 2 is a top plan view of the device of FIG. 1.

Referring now more particularly to the drawings, and specifically to FIGS. 1 and 2 thereof, a dispensing device of the present invention is there generally designated 10, and is shown in FIG. 1 as resting on a horizontal supporting surface or table 11. The device 10 includes generally a horizontally disposed lower part or base 12, and upstanding therefrom is a hollow, upwardly opening receiver 13. The receiver is intended to receive a box of slides or other stacked articles to be dispensed, as will appear more fully hereinafter. A carrier 14 is shiftable horizontally on the upper surface of the base 12, transversely through the receiver 13 between the retracted position shown in FIGS. 1 and 2, and a forwardly extended position.

More specifically, the base 12 may be fabricated essentially of sheet material, including a generally rectangular major, central part or bed 20 from opposite side edges of which depend integral extensions or legs 21. From the lower edge of each leg 21, laterally outstanding therefrom are extensions or wings 22, and a plurality of pads or feet 23 may be secured to the underside of the wings 22 adjacent to the extremities or corners thereof. That is, the pads or feet 23 are arranged in a rectangular outline configuration for bearing engagement with a supporting surface or table 11, and the legs 21 support the bed 20 of base 12 generally horizontally in elevated relation over the surface 11.

The box receiver 13 may also be fabricated of sheet metal, or other suitably stiff sheet material, and may include a generally vertically upstanding front wall 25, generally normal to the bed 20 and extending laterally thereof terminating adjacent to and spaced inward of leg parts 21. From each lateral extremity of front wall 25, integral therewith, there extends rearwardly a vertically disposed side wall 26, which walls are generally parallel to each other and normal to the front wall. A pair of rear wall sections 27 extend in generally coplanar relation with each other from rear edges of respective side walls 26 laterally inwardly, generally normal to the base bed or plate 20, and terminate short of each other. The box receiver 13 is located on the bed plate 20, spaced between the forward edge 28 and the rearward edge 29 of the plate, with the front and rear receiver walls 25 and 26 extending in general parallelism with the front and rear plate edges.

Mounting the receiver 13 on the bed plate 20 of base 12 are a pair of mounting brackets, each including a generally horizontal sheet part or flange 31 seated on the bed plate 20 along a respective receiver side wall 26, and suitably secured to the bed plate, as by a rivet 32. Upstanding from each bracket element or flange 31, closely along the interior of the adjacent receiver side wall 26, and suitably secured thereto, is a generally vertical bracket element or flange 33. The flanges 33 may be welded, or otherwise suitably secured in facing engagement with the adjacent receiver side walls 26; and, the upper edge 35 of each flange 33 extends generally horizontally and defines a ledge, shoulder or box support, as will appear presently.

The front wall 25 of receiver 13 may have its lower region open or cut away, as by a laterally extending, generally rectangular opening or cutout 36. The front wall opening 36 may extend laterally substantially between the flanges 33, and through the lower edge of the front wall to the base bed or plate 20.

Each of the rear wall parts 27 may have its lower edge, as at 37, generally coplanar with the lower edge of the adjacent receiver side wall 26, and thereby spaced over the base plate 20 by the thickness of flange 31, on which the lower edge of the side wall rests. Additionally, extending upwardly from the lower edge 37 of each rear wall part 27, adjacent to and spaced inwardly from the associated side wall 26, is a generally vertical slot 38.

The carrier 14 may also be formed of an integral piece of sheet metal, including a laterally extending upstanding forward or retaining wall 40. Extending from the lower edge of the retaining wall 40, horizontally forwardly for sliding movement on the upper surface of the base plate may be a manually actuable tab or operating member 41.

The front carrier wall or retaining member 40 terminates at its laterally opposite ends short of the extremities of opening 36, as best seen in FIG. 1; and from opposite ends of the front wall 40 there extend rearwardly in parallelism with each other a pair of facing, generally vertically disposed, ribs or flanges 42. The ribs or flanges 42 each lie in a generally vertical plane, and extend slidably through a respective slot 38. The upper surface or edge 45 of each rib or flange 42 is generally coplanar and a flush extension of the upper edge 46 of the carrier front wall 40. At the rear end of each rib or flange 42, remote from the carrier front wall 40, there upstands from the upper rib edge, coplanar with the rib, a stop member or lug 47, which extends to an elevation beyond the height of associated slot 38, to preclude passage therethrough. Also, spaced rearwardly from the carrier front wall 40, the upper edge of each rib or flange 42 is provided with a forwardly facing abutment or shoulder 49, see FIG. 4. The shoulder 49 may be considered as a raised rearward portion or land on its rib or flange 42, extending rearwardly to the associated stop 47, and including a generally horizontal upper surface or edge 50 at an elevation spaced between that of edge 45 and the upper extremity 51 of stop lug 47. The elevation of shoulder surface 50 is less than the upper end of slot 39, so that the ribs or flanges 42 may shift forwardly through the slots, until limited by abutting engagement of the stop lugs 47 with the rear surfaces of the receiver rear wall parts 27.

In addition, the upstanding ribs 42 are each provided with laterally outstanding guide members or flanges 55, each extending generally horizontally outwardly from the lower edge of a respective rib or flange 42. The guide members or flanges 55 are slidable on and in facing engagement with the base plate 20, and extend laterally outwardly to terminate in generally parallel outer edges 56 which are slidably engageable with respective internal bracket flanges 33 to effectively guide the carrier 14 in its forward and rearward translatory motion, without jamming or cocking.

In FIGS. 3 and 4 are shown a container or box 60, which may have its lower end open and inserted conformably downwardly into receiver 13 through the open upper end of the latter. The open lower end of box 60 may terminate in downwardly facing wall edges 59 supported by the upwardly facing ledges 35 of flanges 33. This spaces the lower open box edge sufficiently spaced above the upper edge or surface 45 of each rib 42 to permit the gravitational deposit on the edge surfaces 45 of a slide or lowermost stacked article completely exteriorly of the box.

That is, a stack of slides 61, 62, 63 and 64 are shown in the lower open region of box 60, the lowermost slide 61 resting on the upper edge surfaces 45 of ribs 42 and being entirely exteriorly of the box 60, which is supported on the ledges 35. Also, the opening 36 in front receiver wall 25 is sufficiently spaced over the upper edge surfaces 45 to permit the passage through opening 36 of a single lowermost slide 61 on the surface 45, and the retention in the stack of the next lowermost slide 62.

The pusher surface or shoulder 49, spaced just rearwardly of the stack of articles 61–64, engages the lowermost article 61 to shift the latter forwardly and outwardly through front wall opening 36 upon shifting movement of the carrier 14 to the forwardly extended position shown in dashed outline in FIG. 4. The height of the pusher element or shoulder 49 is less than the thickness of a single article 61–64, so that only the lowermost article 61 is displaced forwardly and exteriorly of the receiver 13. Simultaneously, the shoulder surfaces or lands 50 engage beneath the next lowermost article 62 to support the latter and the superposed articles of a stack until the carrier is returned rearwardly, whereupon the then lowermost article and stack may fall onto the rib surfaces 45, for repetition of the above described procedure.

It will be apparent in the extended phantom position of FIG. 4, that the stop lugs 47 are in aubtting engagement with the rear wall parts 27 to limit the carrier 14 to a forwardly extended position with the lowermost slide dispensed substantially completely exteriorly of the receiver 13. The slide may then be readily removed, either by an operator's fingers engaging the slide edges, or by a tool, to protectively handle the dispensed slide. Also, in the absence of articles in the receiver 13, and retraction of the carrier 14 to a limiting inward position, the front or retaining wall 40 will engage with lower inner portions of the back wall parts 27 to retain the carrier assembled with the receiver and base.

From the foregoing, it is seen that the dispenser device of the present invention is extremely simple in construction for extreme reliability and long useful life, and otherwise fully accomplishes its intended objects.

Although the present invention has been described in some detail by way of illustration and example for purposes of clarity of understanding, it is understood that certain changes and modifications may be made within the spirit of the invention.

What is claimed is:

1. A dispensing device for dispensing articles from a boxed stack wherein a box has its lower end open, said device comprising a base, a box receiver upstanding from said base and having an upper opening for removably receiving the lower open end of a box, a pair of upwardly facing ledges in said receiver at opposite sides thereof for supporting engagement with laterally opposite open end edges of a received box without obstructing the lower open end of the received box, an article carrier extending transversely through a lower region of said receiver between said ledges and shiftable into and out of a retracted position beneath a box for receiving a lowermost article, shoulder means upstanding from said carrier for pushing engagement with the lowermost article on said carrier during carrier movement from its retracted position to an extended position with the previously lowermost article entirely exteriorly of the receiver, and stop means on said carrier and engageable with said receiver to limit carrier movement to said extended position for convenient removal of the article, said carrier comprising a pair of generally parallel spaced upstanding ribs extending longitudinally of carrier shifting movement, and said stop means upstanding from said carrier externally of said receiver and abuttingly engageable therewith to limit said carrier movement.

2. A dispensing device according to claim 1, said shoulder means comprising a land on each rib extending generally toward said stop means for location beneath a lowermost article when a previously lowermost article is exteriorly of said receiver.

3. A dispensing device according to claim 1, said ribs being spaced inwardly from adjacent walls of said receiver, and guide flanges extending outwardly from said ribs for sliding engagement with said base.

4. A dispensing device according to claim 2, said ledges being in a plane spaced above said article carrier ribs a distance greater than the height of a single article and less than the height of two articles, for horizontally passing the lowermost article from the lower box end and horizontally retaining the next lower article.

* * * * *